(12) United States Patent
Missfeldt

(10) Patent No.: US 6,221,574 B1
(45) Date of Patent: *Apr. 24, 2001

(54) CYANINE DYES

(75) Inventor: Michael Missfeldt, Leichlingen (DE)

(73) Assignee: Agfa-Gevaert N.V. (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/408,107

(22) Filed: Sep. 29, 1999

(30) Foreign Application Priority Data

Oct. 5, 1998 (DE) .............................................. 198 45 642

(51) Int. Cl.⁷ ................ G03C 1/14; G03C 1/16; G03C 1/20
(52) U.S. Cl. .......................... 430/583; 430/574; 430/584; 430/585; 430/592
(58) Field of Search .................................... 430/581, 583, 430/584, 585, 592, 574

(56) References Cited

U.S. PATENT DOCUMENTS 5,919,613 * 7/1999 Missfeld .............................. 430/583

FOREIGN PATENT DOCUMENTS 599 383   6/1994 (EP) .

* cited by examiner

*Primary Examiner*—Thorl Chea
(74) *Attorney, Agent, or Firm*—Connolly Bove Lodge & Hutz LLP

(57) ABSTRACT

The present application provides cyanine dyes of the formula (I)

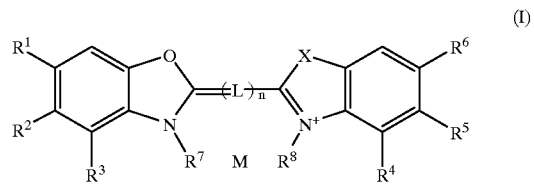

in which
$R^1$, $R^2$, $R^3$, $R^4$, $R^5$ and $R^6$ mutually independently denote a substituent, providing that at least one of the residues $R^1$, $R^2$, $R^3$ denotes an indolyl substituent, X denotes O, S, Se, $NR^9$, CH=CH or $C(CH_3)_2$, wherein $R^9$ denotes a optionally substituted alkyl residue, $R^7$, $R^8$ mutually independently denote alkyl, sulfoalkyl, carboxyalkyl, $-(CH_2)_l-SO_2-Y-SO_2$—alkyl, $-(CH_2)_l-SO_2-Y-CO$—alkyl, $-(CH_2)_l-CO-Y-SO_2$—alkyl, $-(CH_2)_l-CO-Y-O$—alkyl or $-(CH_2)_l-NH-SO_3^\ominus$, $-(CH_2)_l-N(alkyl)-SO_3^\ominus$ or $-(CH_2)_l-N(aryl)-SO_3^\ominus$, providing that l=1 to 6 and Y means NH or $N^-$, n means 1, 3, 5, 7, L denotes a substituted or unsubstituted methine group, which may be a constituent of one or more carbocyclic rings, and M denotes a counterion optionally necessary to equalise charges, as well as color photographic materials containing cyanine dyes of the formula (I) and the use of compounds of the formula (I) as spectral sensitizers.

9 Claims, No Drawings

CYANINE DYES

This invention relates to cyanine dyes of the formula (I), and to a colour photographic material which contains cyanine dyes of the formula (I) and to the use of compounds of the formula (I) as spectral sensitisers.

Improving the spectral sensitivity of photographic materials is a constant challenge. It is known to use polymethine dyes, to extend sensitivity beyond the intrinsic sensitivity range of the silver halide used. Cyanine dyes are particularly suitable for this purpose.

Cyanines containing benzoxazole comprise one group of cyanine dyes which has been thoroughly investigated. Numerous different cyanines containing benzoxazole are known and are conventionally used in colour photographic materials.

EP 0 599 383 discloses cyanine dyes which, as a constituent of silver halide emulsion layers, in particular avoid the formation of colour spots after processing when tab-grain emulsions are used. These comprise cyanine dyes, the benzo ring of which is linked with a furanyl or pyrrolyl substituent.

There is thus a requirement for cyanine dyes which both have increased spectral sensitivity, especially when used in tab-grain emulsions, and have good storage stability, especially after storage at elevated temperature and elevated humidity.

The object of the present invention is to provide cyanine dyes which are distinguished by particularly elevated spectral sensitivity and simultaneously by good long term storage stability, in particular under tropical conditions.

It has surprisingly been found that cyanine dyes containing benzoxazole according to the formula (I) and having at least one indolyl substituent have outstanding spectral sensitivity combined with good storage stability, in particular under tropical conditions. It has additionally proved possible distinctly to increase the spectral sensitivity of tab-grain emulsions.

The present application provides cyanine dyes of the formula (I)

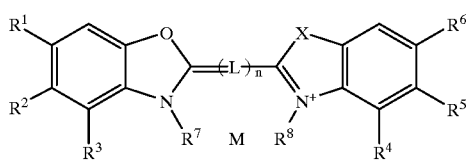

(I)

in which $R^1$, $R^2$, $R^3$, $R^4$, $R^5$ and $R^6$ mutually independently denote a substituent, providing that at least one of the residues $R^1$, $R^2$, $R^3$ denotes an indolyl substituent, X denotes O, S, Se, $NR^9$, CH=CH or $C(CH_3)_2$, wherein $R^9$ denotes a optionally substituted alkyl residue, $R^7$, $R^8$ mutually independently denote alkyl, sulfoalkyl, carboxyalkyl, —$(CH_2)_l$—$SO_2$—Y—$SO_2$—alkyl, —$(CH_2)_l$—$SO_2$—Y—CO—alkyl, —$(CH_2)_l$—CO—Y—$SO_2$—alkyl, —$(CH_2)_l$—CO—Y—O—alkyl or —$(CH_2)_l$—NH—$SO_3$—, —$(CH_2)_l$—N(alkyl)—$SO_3$— or —$(CH_2)_l$—N(aryl)—$SO_3$—, providing that l=1 to 6 and Y means NH or $N^-$, n means 1, 3, 5, 7, L denotes a substituted or unsubstituted methine group, which may be a constituent of one or more carbocyclic rings, and M denotes a counterion optionally necessary to equalise charges.

For the purposes of the present application, unless more specifically defined, a substituent should be taken to mean, for example, H, halogen, preferably F, Cl or Br, aryl, hetaryl, alkyl, alkenyl, $OR^{10}$, wherein $R^{10}$ denotes $C_1$ to $C_6$ alkyl, in particular methyl, ethyl and propyl. A substituent may, however, furthermore comprise fused ring systems, which are optionally substituted. For example, a fused ring system may be formed by $R^6$ with $R^5$ or $R^5$ with $R^4$. Fused ring systems should preferably be taken to mean benzo or naphtho ring systems.

For the purposes of the present application, alkyl should be taken to mean linear or branched, cyclic or straight-chain, substituted or unsubstituted hydrocarbon groups, preferably alkyl groups having 1 to 20 C atoms, in particular 1 to 6 C atoms; open-chain alkyl groups which may be considered are in particular methyl, ethyl, n-propyl, n-butyl and n-pentyl while branched alkyl residues which may be considered are in particular methyl- or ethyl-branched. Alkyl may moreover comprise partially or completely halogenated alkyl groups as substituents, such as in particular $CF_3$ or —$CH_2CF_2CF_2H$.

For the purposes of the present invention, alkenyl should be taken to mean linear or branched, cyclic, substituted or unsubstituted unsaturated hydrocarbon residues, such as for example ethenyl, 2-propenyl.

For the purposes of the present application, unless otherwise defined, aryl should be taken to mean aromatic hydrocarbon groups, wherein they preferably comprise 5- or 6-membered ring systems, which may be in the form of monocyclic or also fused ring systems. These may comprise both substituted and unsubstituted ring systems. Phenyl and naphthyl groups are, for example, particularly preferred. Substituents which may be considered are the compounds already mentioned, preferably halogen, alkyl and $OR^{10}$ with the above-stated meaning.

For the purposes of the present application, unless otherwise defined, hetaryl should be taken to mean aromatic systems which contain at least one heteroatom. These may comprise both substituted and unsubstituted ring systems. Typical examples are pyridine, pyridazine, pyrimidine, pyrazines, oxazole, isoxazole, thiazoles, 3,4-oxadiazole, 1,2,4-oxadiazole, imidazole, 1,2,3-triazole, 1,2,4-triazole; particularly preferred heterocyclic substituents are 2-furanyl, 3-furanyl, N-pyrrolyl, 2-pyrrolyl, 3-pyrrolyl, 2-thienyl, 3-thienyl and N-indolyl.

For the purposes of the present invention, unless otherwise defined, counterions M which may be considered, depending upon the substituents and thus charge relationships, are for example the following compounds: tosylate, $I^-$, $Br^-$, $Cl^-$, preferably diazabicyclooctane-$H^+$ ($DABCOH^+$) or diazabicycloundecane-$H^+$ ($DBUH^+$), in particular $Na^+$, $Li^+$, $K^+$ and particularly preferably $Et_3N^+H$.

n denotes 7, preferably 5, in particular 1 or 3.

L may, for example, denote =C— or, as a constituent of a ring system

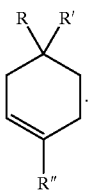

The following combinations for

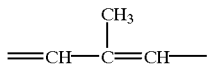

may arise from the above: for n=1, =C— is preferred, for n=3

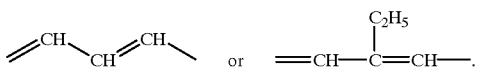

or preferably

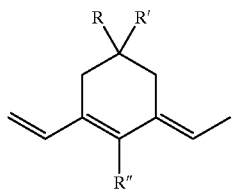

wherein R and R' preferably denote H or alkyl and R" denotes H, halogen, N(alkyl)$_2$, N(aryl)$_2$, 5-membered nitrogenous heterocyclics, such as pyrrole or pyrrolidine or S-alkyl. For n=7

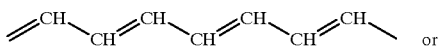

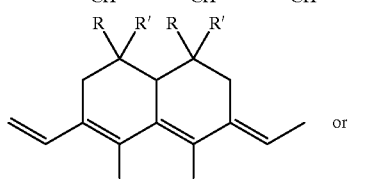

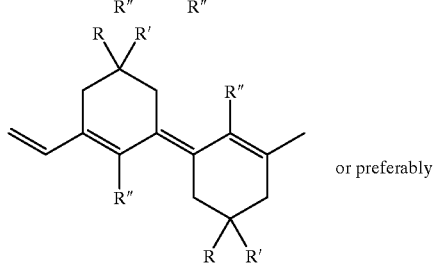

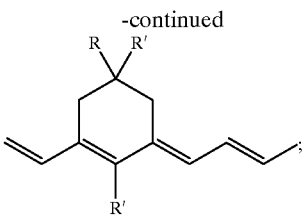

residues R, R' and R" are defined as already stated above.

Particularly preferred compounds of the formula (I) are the compounds of the formulae (Ia), (Ib) and (Ic) listed below:

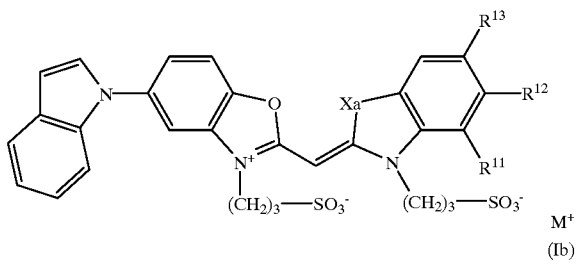

(Ia)

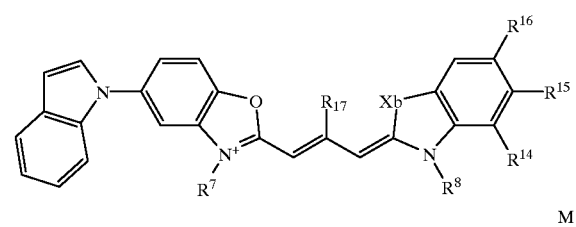

(Ib)

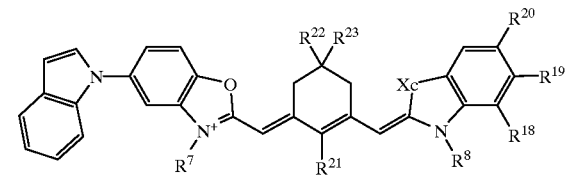

(Ic)

in which $X_a$, $X_b$ and $X_c$ denote O, S, Se, $NR^9$, CH=CH or $C(CH_3)_2$, wherein $R^9$ denotes an optionally substituted alkyl residue; preferably, $X_a$ denotes S, O, $X_b$ denotes O, S, N—$C_2H_5$, Se and $X_c$ denotes S, Se or O, $R^{11}$ to $R^{16}$ and $R^{18}$ $R^{20}$ denote a substituent, preferably H, halogen, in particular F, Cl or Br, a substituted or unsubstituted 1-, 2- or 3-pyrrolyl, 2- or 3-thienyl, N-indolyl, phenyl or 2- or 3-furanyl residue, alkyl, preferably having 1 to 6 C atoms, in particular methyl, ethyl or propyl, $R^{11}$ and $R^{12}$ or $R^{12}$ and $R^{13}$ or $R^{14}$ and $R^{15}$ or $R^{15}$ and $R^{16}$ or $R^{18}$ and $R^{19}$ or $R^{19}$ and $R^{20}$ may be a constituent of a fused benzo or naphtho ring, $R^{17}$ denotes H, $CH_3$ or $C_2H_5$ $R^{21}$ preferably denotes halogen, in particular Cl, as well as N(alkyl)$_2$, N-piperidinyl, N-pyrrolidinyl, N-pyrrolyl, as well as S-alkyl, in particular $SCH_3$ or S(CH$_2$)$_m$COOH, providing that m denotes 1, 2, 3, 4, 5 or 6, R$^{22}$ and R$^{23}$ denote H or alkyl, in particular methyl, or carboxylic acid or carboxylic acid ester residues, R$^7$ and R$^8$ have the above-stated meaning and mutually independently preferably denote ethyl, sulfoethyl, sulfopropyl, sulfobutyl, 3-methylsulfopropyl and

M may, where required, denote a counterion, preferably Na$^+$, EtN$^+$H, tosylate and I$^-$.

A typical list of particularly preferred compounds according to the present invention is shown below:

I-1
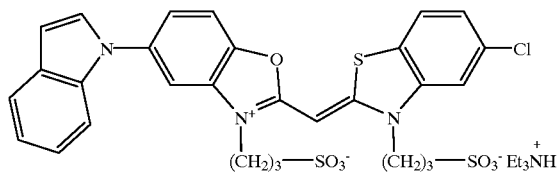

I-2
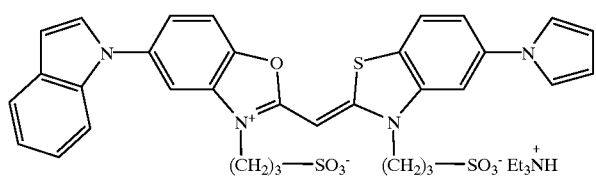

I-3
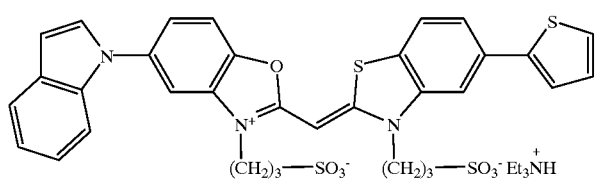

I-4
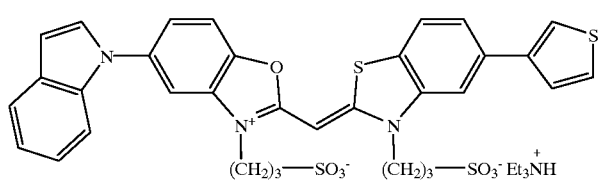

I-5
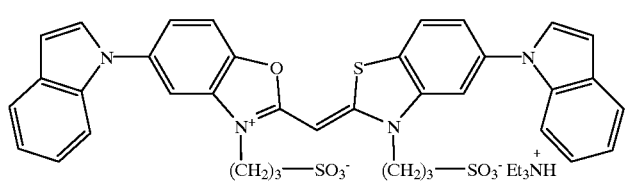

I-6
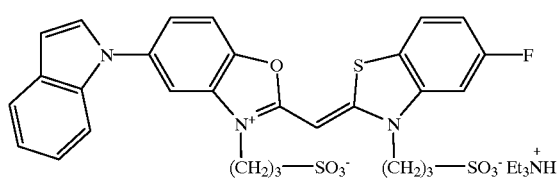

I-7
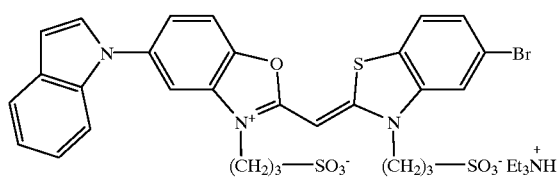

-continued
I-8
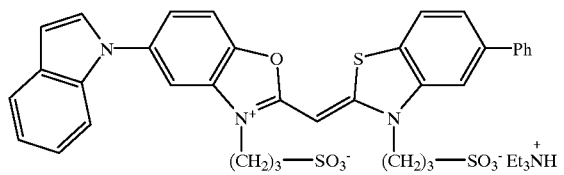
I-9
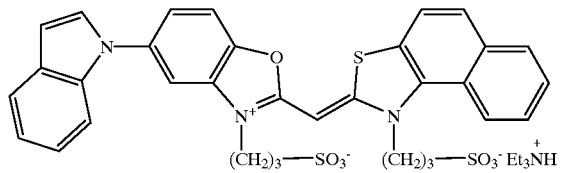
I-10
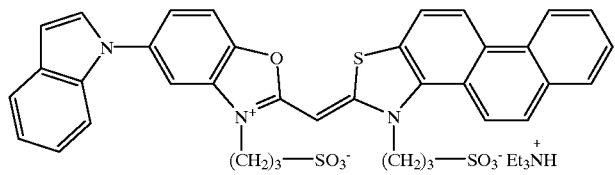
I-11
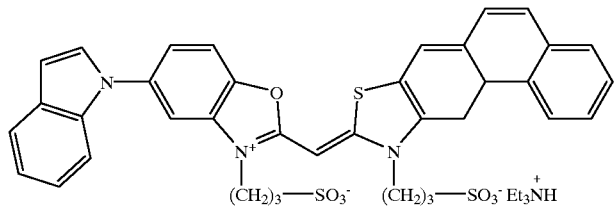
I-12
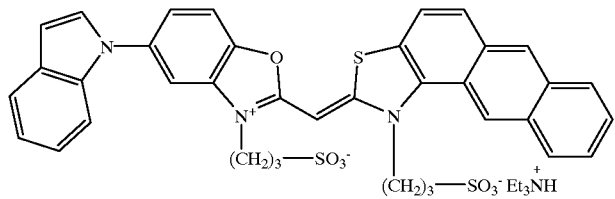
I-13
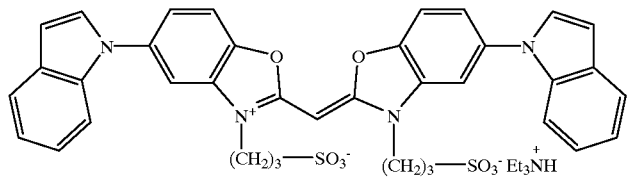
I-14
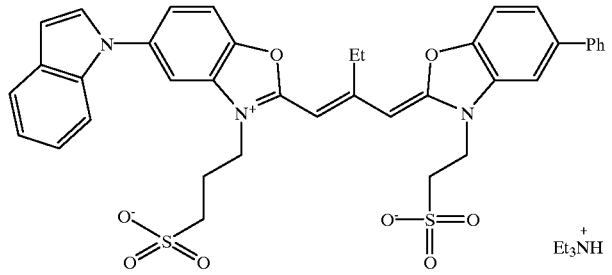

-continued
I-15
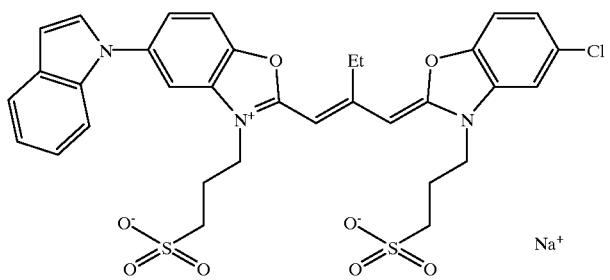
I-16
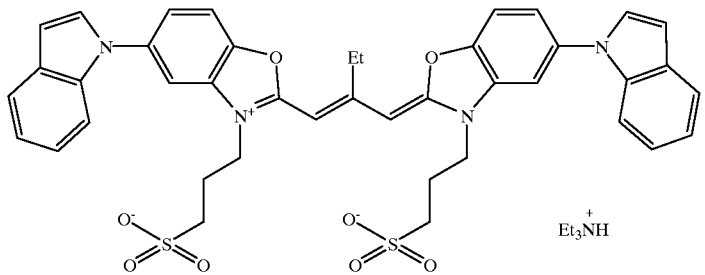
I-17
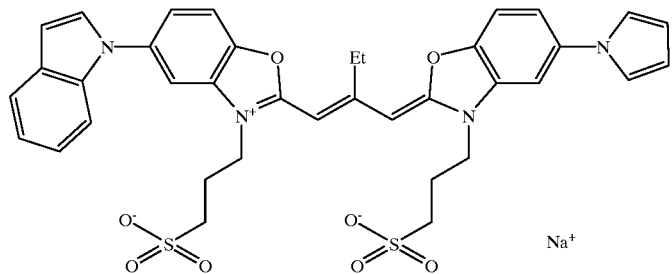
I-18
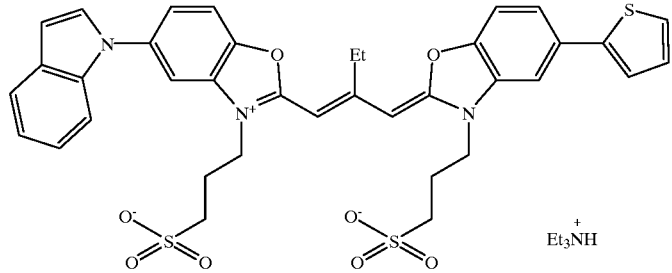
I-19
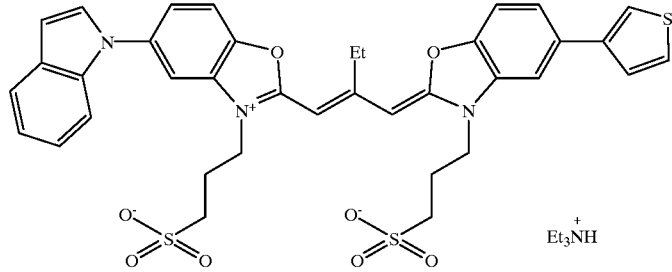

-continued
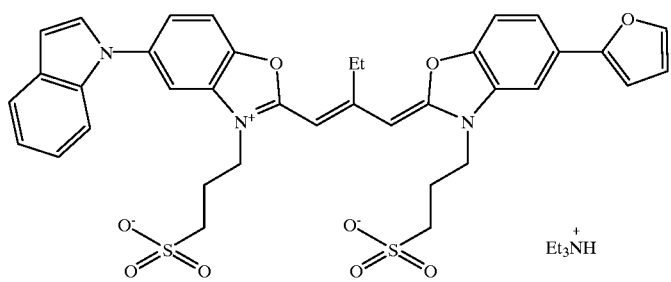
I-20
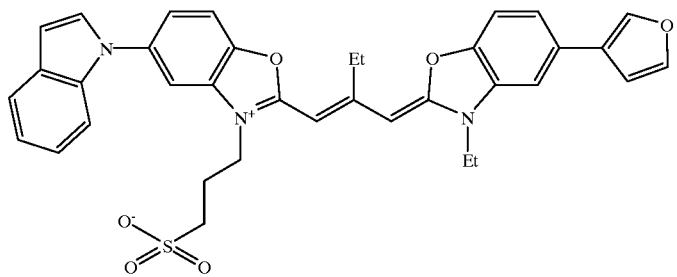
I-21
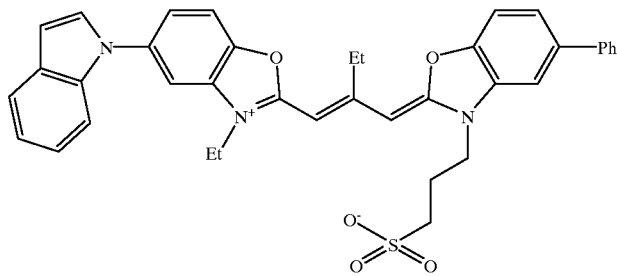
I-22
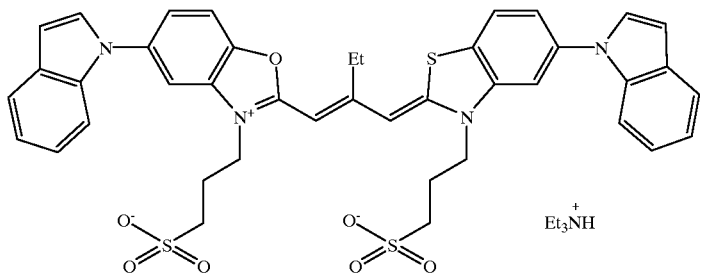
I-23
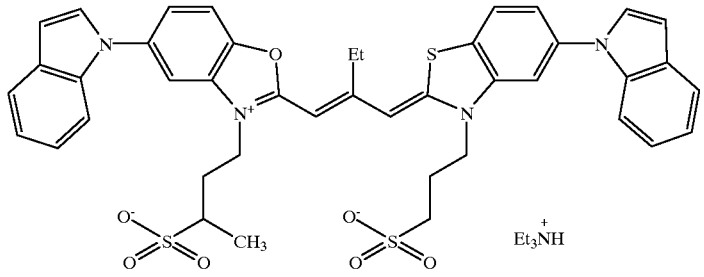
I-24

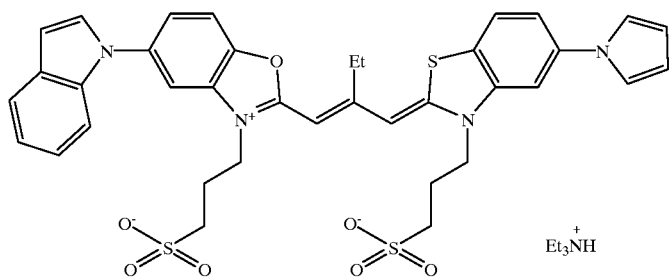
I-25
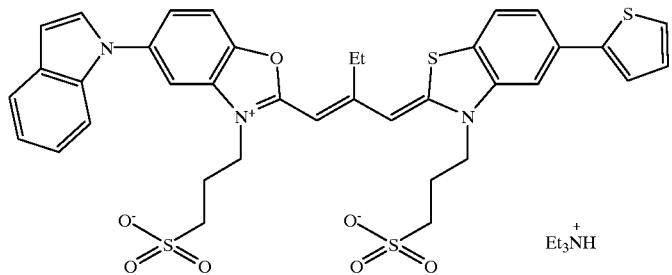
I-26
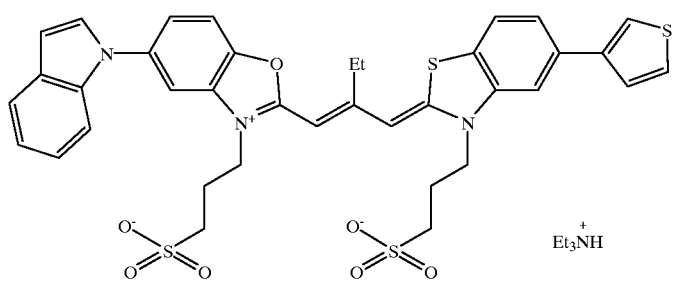
I-27
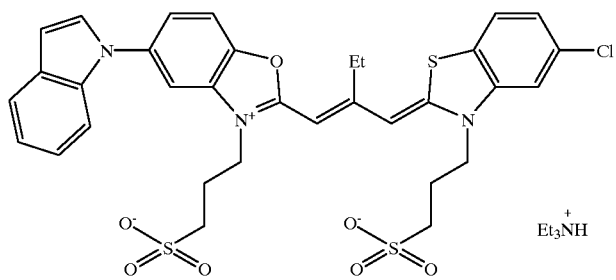
I-28
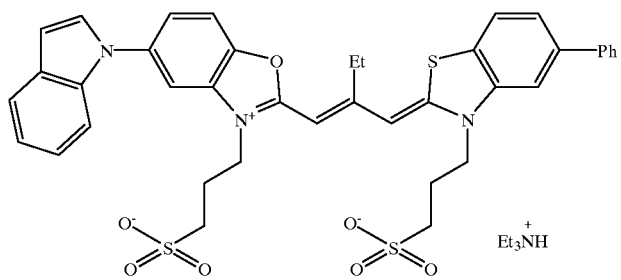
I-29

I-30
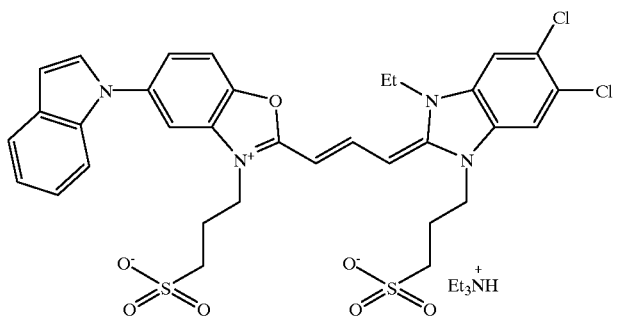
I-31
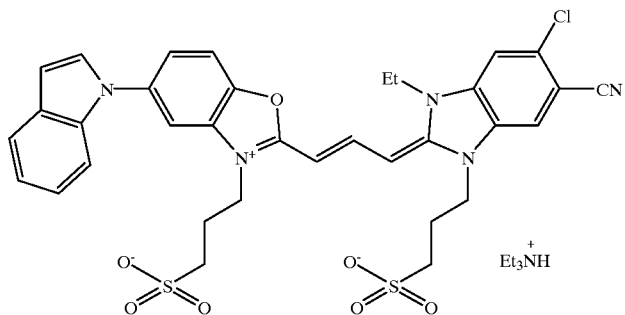
I-32
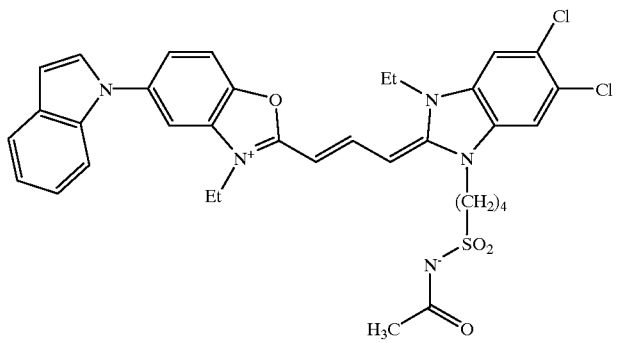
I-33
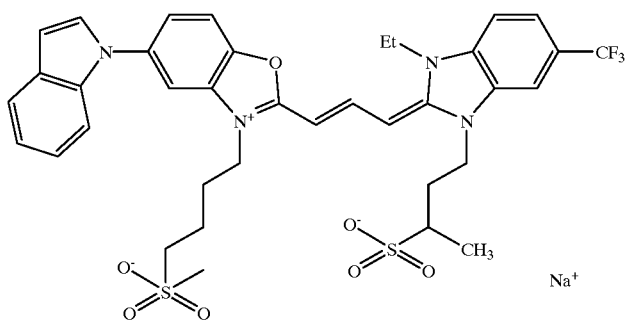

-continued
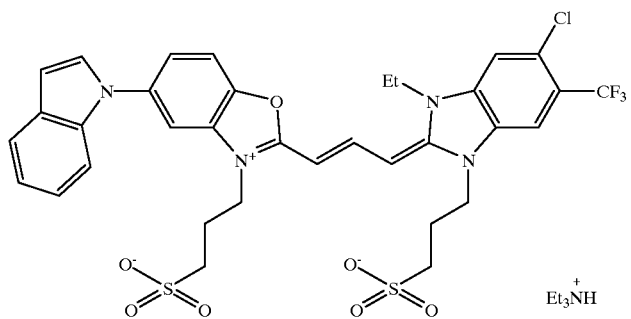
I-34
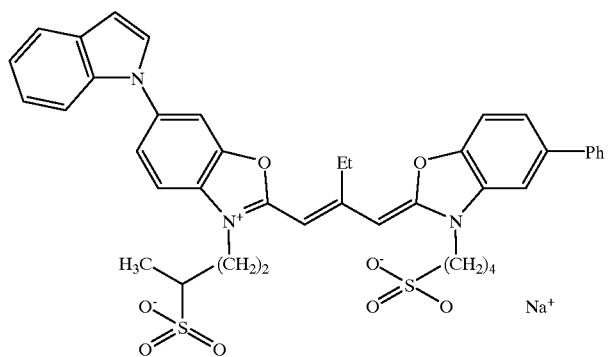
I-35
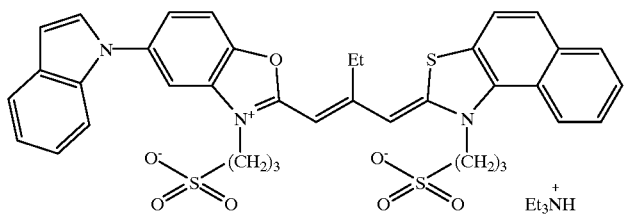
I-36
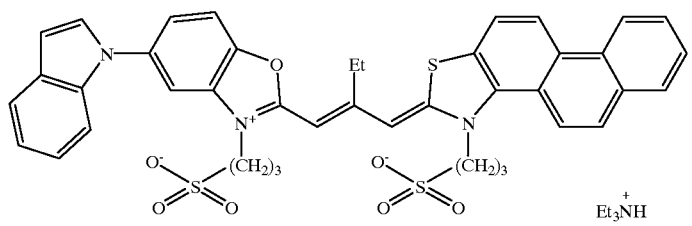
I-37
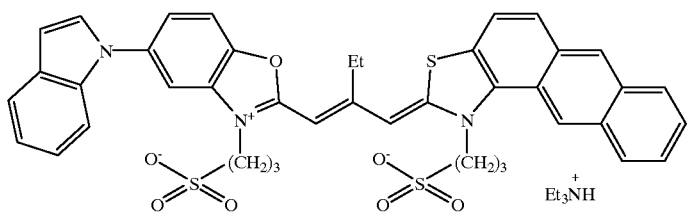
I-38
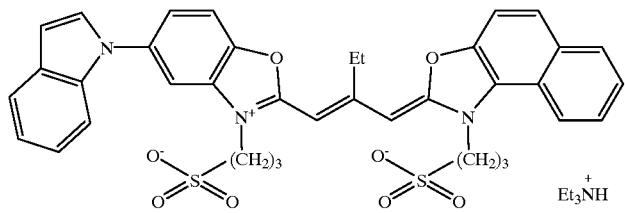
I-39

I-40
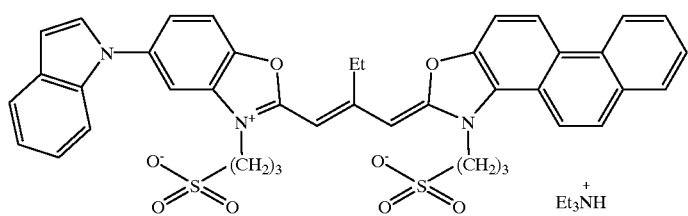
I-41
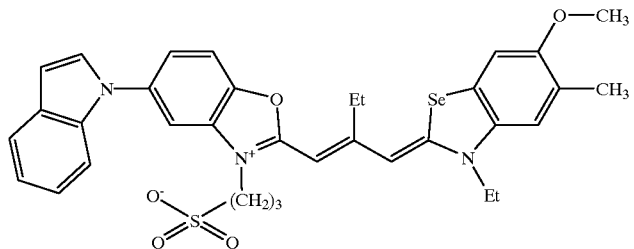
I-42
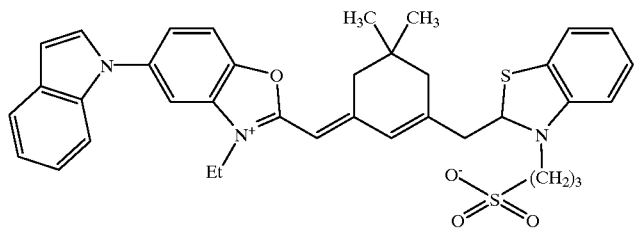
I-43
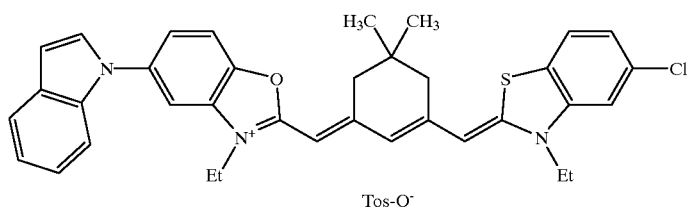
I-44
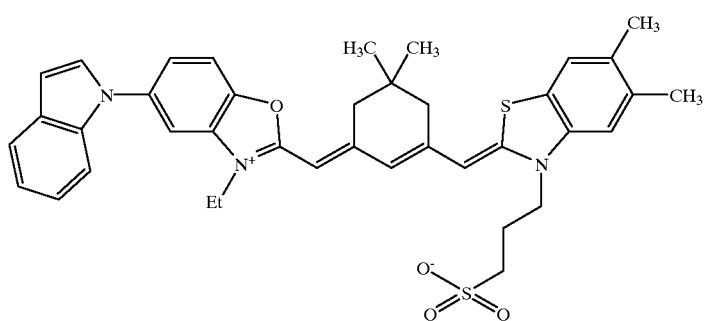
I-45
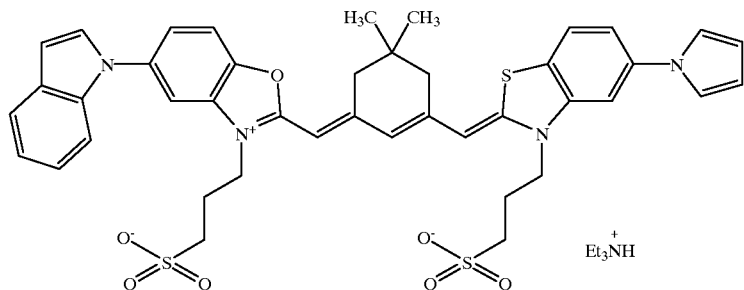

I-46
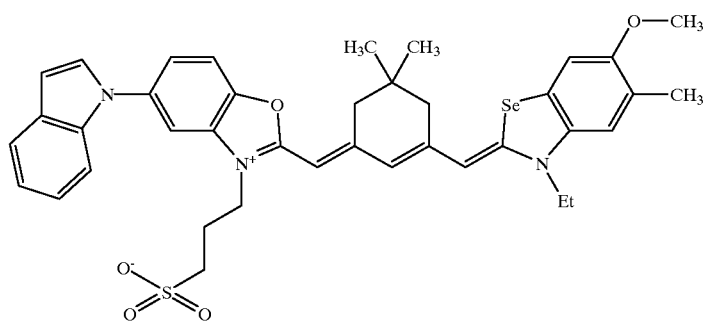
I-47
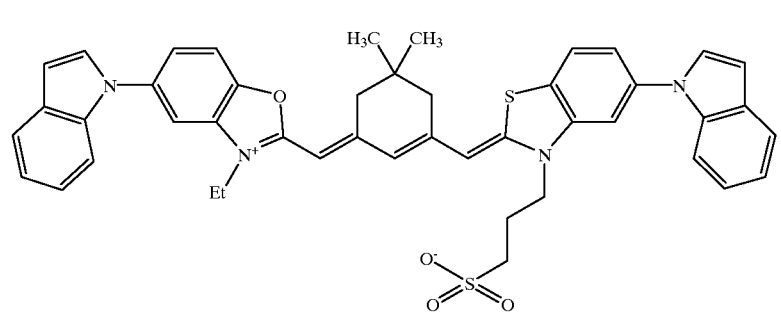
I-48
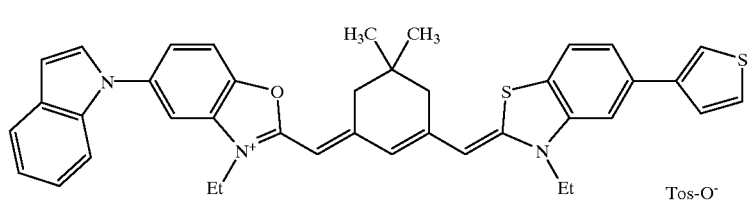
I-49
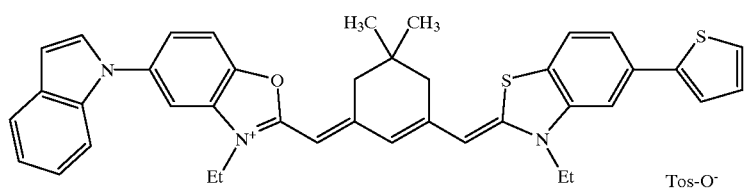
I-50
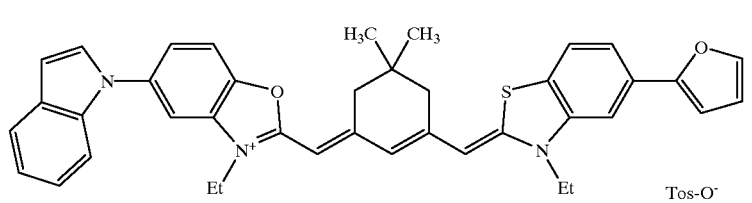
I-51
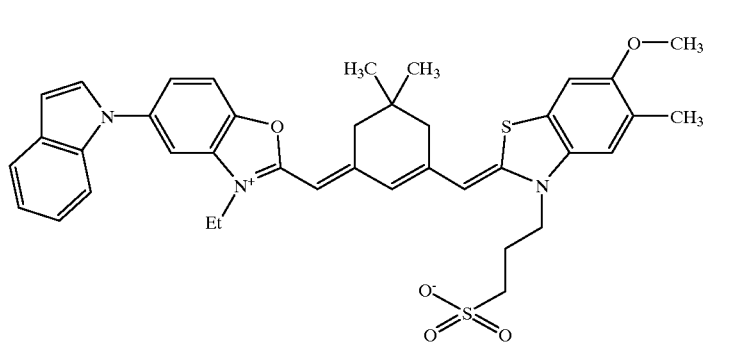

-continued
I-52
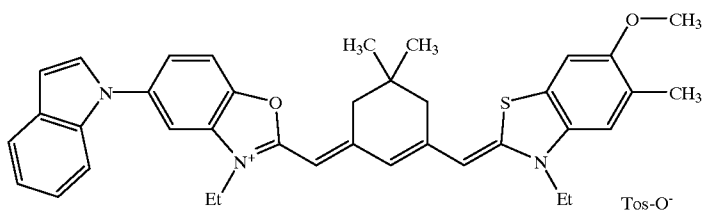
I-53
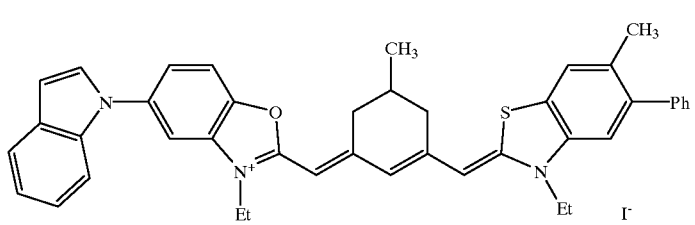
I-54
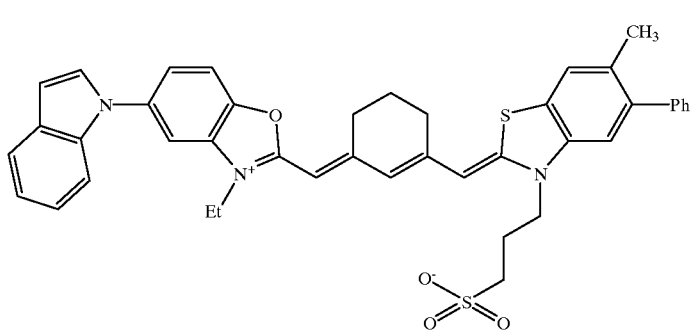
I-55
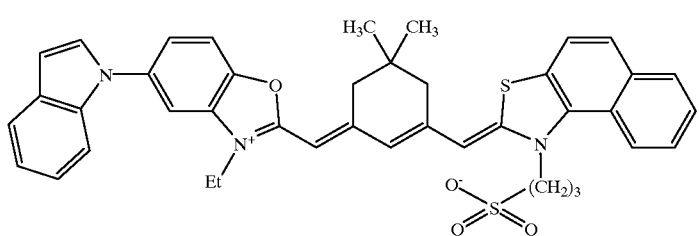
I-56
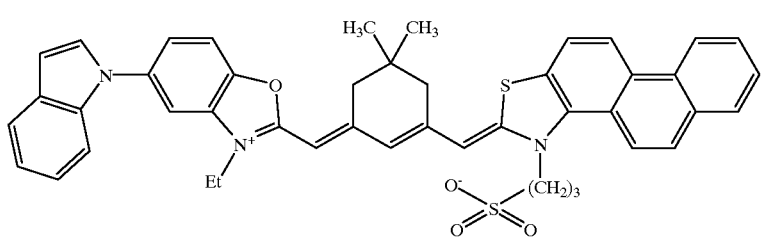
I-57
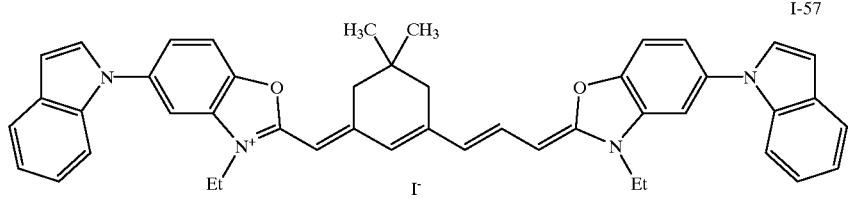

-continued

I-58

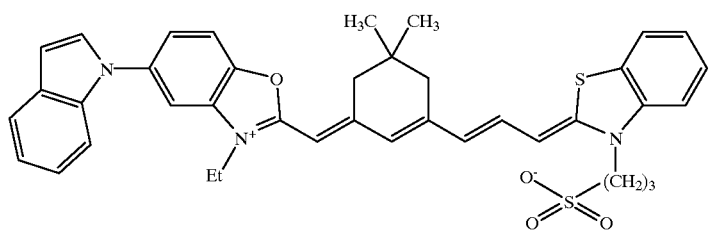

In the formulae I-1 to I-15, "Et" means $C_2H_5$ and "Ph" means phenyl.

The cyanine dyes according to the invention may be synthesised in an analogous manner to production processes known from the literature:

Synthesis of Dye (I)-16

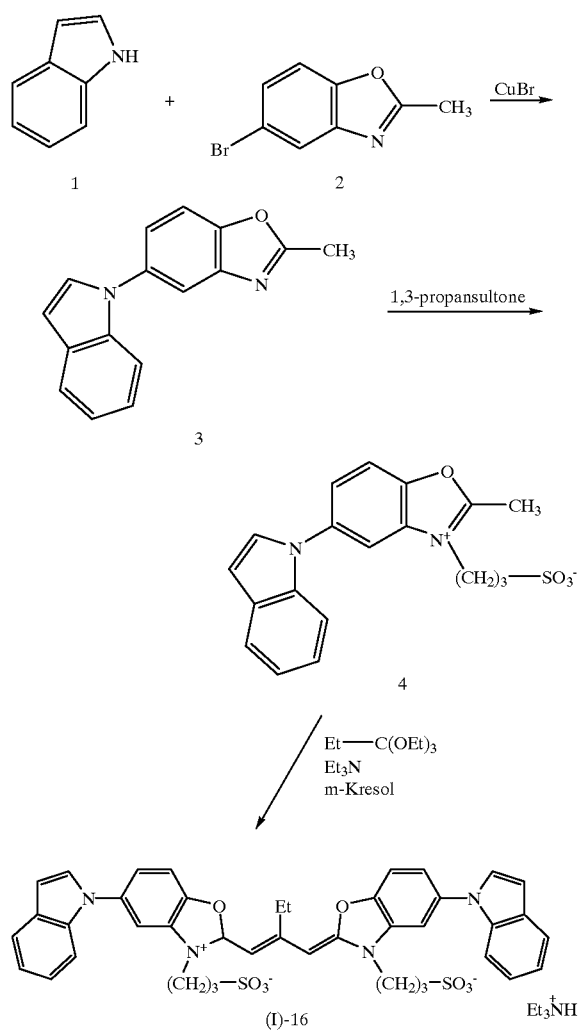

3 was synthesised from 1 and 2 in an analogous manner to the method described in *J. Chem. Soc., Perkin Trans.*, 1989, 2407.

Production of the Quaternary Salt 4

2.48 g (10 mmol) of 3 are heated to 165° C. for 8 hours in 5 ml of dichlorobenzene with 1.22 g (10 mmol) of 1,3-propanesultone. After cooling to room temperature, 30 ml of acetone are added, the mixture is refluxed for 2 hours, allowed to cool to room temperature, suction filtered, thoroughly rewashed with acetone and, without intermediate drying, extracted for 1.5 h with 20 ml of methanol. Yield: 2.23 g (60.2% of theoretical)

Production of the Dye (I)-16

3.7 g (10 mmol of 4 are dissolved in 10 ml of m-cresol with heating and then combined at an internal temperature of approx. 100° C. with 5.29 g (30 mmol) of orthopropionic acid triethyl ester and stirred for 15 minutes at 100° C. After cooling to room temperature, a solution of 3.7 g (10 mmol) of 4, dissolved in 10 ml of m-cresol, is added and 1.78 ml (12.8 mmol) of triethylamine are apportioned at room temperature within 5 minutes. After 2 hours' stirring at room temperature, the dye solution is introduced into 75 ml of acetone within 45 minutes. The dye is left to crystallise out overnight, is suction filtered and thoroughly rewashed with acetone. The crude dye is dissolved in 60 ml of formamide with heating, combined with 30 ml of acetone, hot-filtered and again combined with 150 ml of acetone. The dye is left to crystallise out overnight, is suction filtered and thoroughly washed with acetone. After drying to constant weight under a vacuum at 50° C., 3.9 g (44.3% of theoretical) of dye are obtained.

The cyanines according to the invention may also be produced by using the synthesis methods which are described in *"The Cyanine Dyes & Related Compounds"* by Frances M. Hamer, Interscience Publishers (1964).

The sensitising dyes according to the invention bring about sensitisation which not only results in elevated sensitivity but is also stable in the blue range of the spectrum between 390 and 510 nm, in the green range of the spectrum between 520 and 590 nm, in the red range of the spectrum between 590 and 680 or 680 to 750 nm and in the infra-red range of the spectrum. Stable sensitisation should here be taken to mean that after storage even under tropical conditions, which for the purposes of the present invention should be taken to mean storage at 35° C. and 90% relative atmospheric humidity for 7 days, the spectral sensitivity of the sensitising dyes according to the invention remains largely unchanged.

In a particularly preferred embodiment, at least one cyanine dye according to the invention is used together with at least one dye of the formula (II)

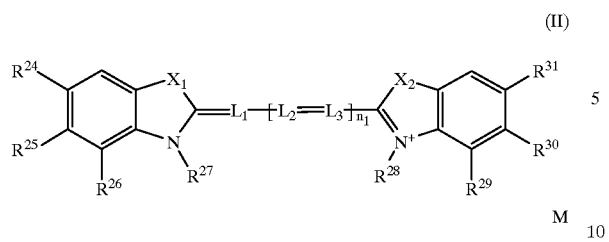

(II)

wherein $X_1$, $X_2$ mutually independently denote O, S, Se, $NR^9$, $C(CH_3)_2$ or CH=CH, wherein $R^9$ denotes an optionally substituted alkyl residue, $R^{27}$, $R^{28}$ mutually independently denote alkyl, sulfoalkyl, carboxyalkyl, —$(CH_2)_1$—$SO_2$—Y—$SO_2$—alkyl, —$(CH_2)_1$—$SO_2$—Y—CO—alkyl, —$(CH_2)_1$—CO—Y—$SO_2$—alkyl, —$(CH_2)_1$—CO—Y—CO—alkyl, providing that l =1–6, Y means NH or $N^-$, $R^{24}$, $R^{25}$, $R^{26}$, $R^{29}$, $R^{30}$ and $R^{31}$ mutually independently denote halogen, H, alkyl, alkoxy, phenyl, 2-thienyl, 3-thienyl, 1-pyrrolyl, 2-furanyl, 3-furanyl, CN, $CF_3$, aryl; or $R^{24}$ together with $R^{25}$ or $R^{25}$ together with $R^{26}$ or $R^{29}$ together with $R^{30}$ or $R^{30}$ together with $R^{31}$ denote the remaining members to complete an optionally substituted fused benzo or naphtho ring system, $n_1$ means 0, 1, $L_1$, $L_2$, $L_3$ mutually independently denote substituted or unsubstituted methine groups and M denotes a counterion optionally necessary to equalise charges.

Suitable compounds of the formula II are:

(II)-1

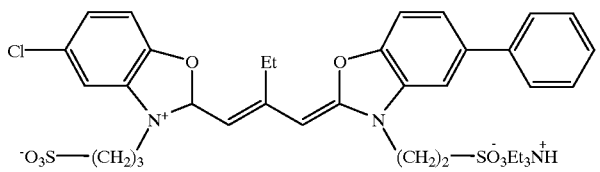

(II)-2

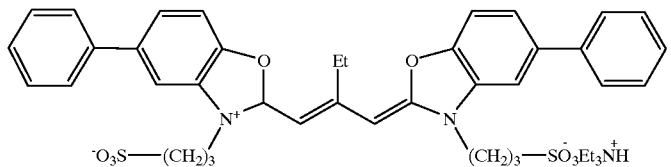

(II)-3

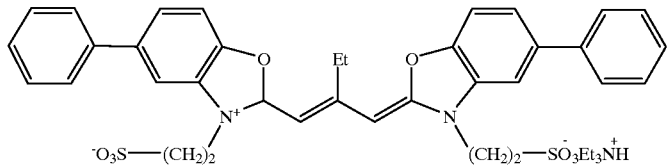

(II)-4

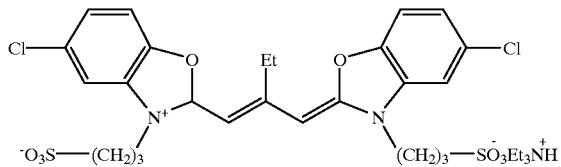

(II)-5

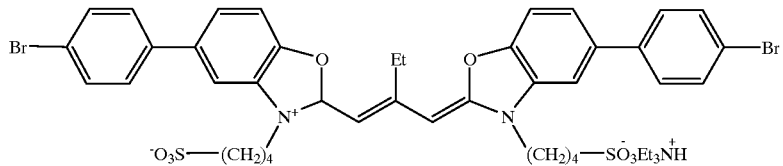

(II)-6

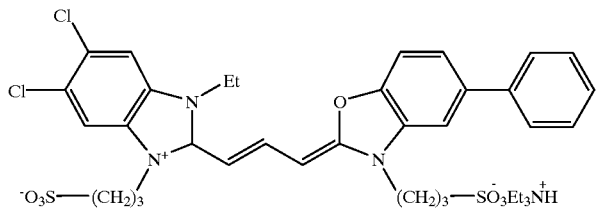

(II)-7
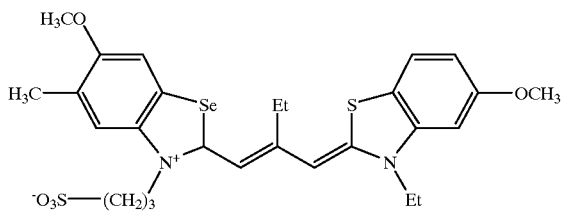
(II)-8
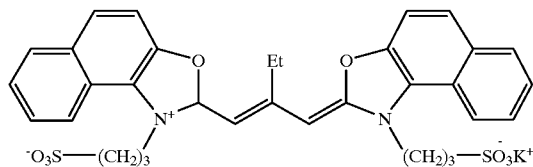
(II)-9
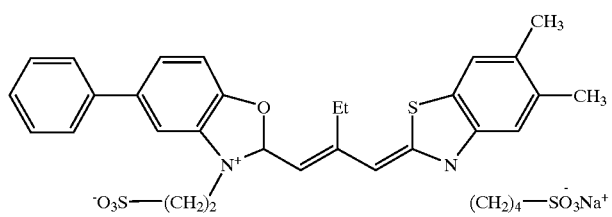
(II)-10
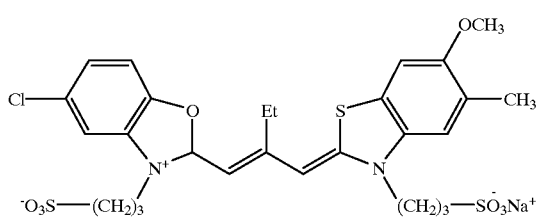
(II)-11
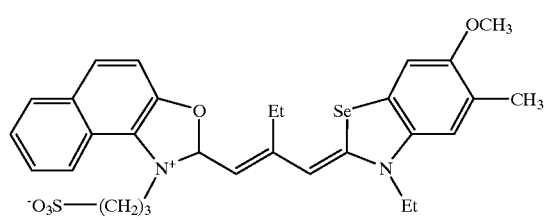
(II)-12
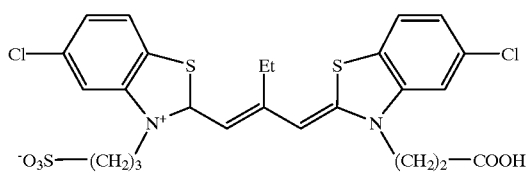
(II)-13
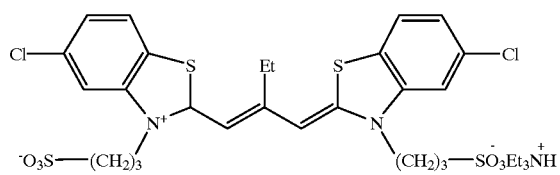
(II)-14
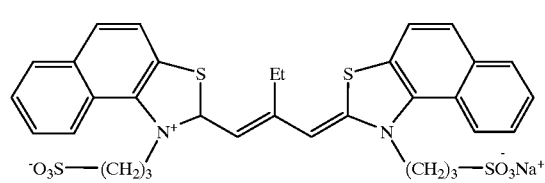
(II)-15
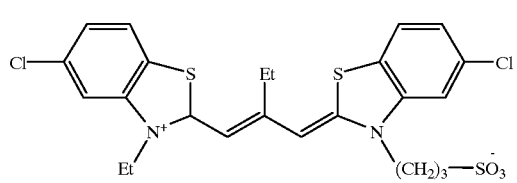
(II)-16
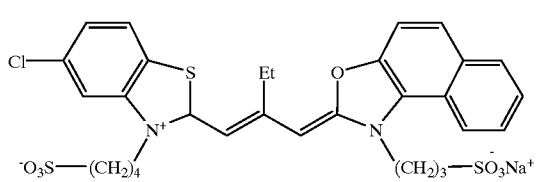
(II)-17
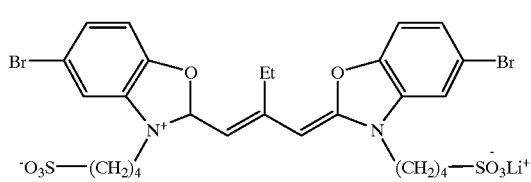

(II)-18

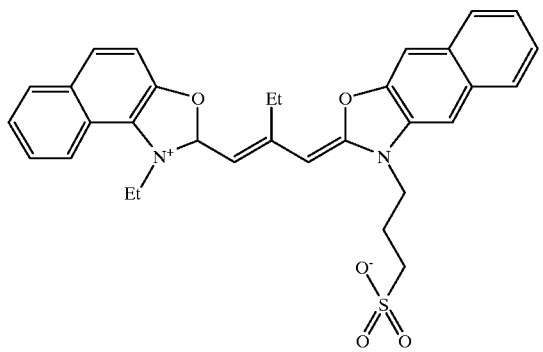

(II)-19

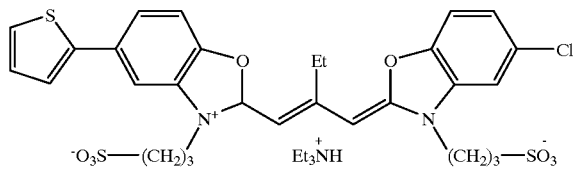

(II)-20

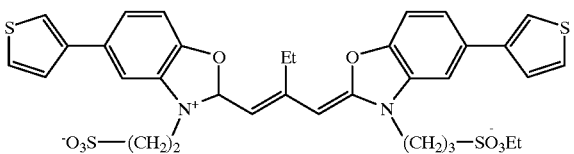

By joint use of compounds of the formulae (I) and (II), it is possible to achieve still higher spectral sensitivity, combined with particularly good storage stability, in particular with regard to tropical stability. According to the invention, the compounds (I) and (II) are preferably present in a mixture ratio of 0.1:10 to 10:0.1. A mixture ratio of the compounds of the formula (I) to those of the formula (II) of 10:1 to 1:10 is particularly preferred.

According to the present invention, at least one compound of the formula (I) is used, preferably three compounds of the formula (I) are used. As mentioned above, a blend with compounds of the formula (II) is particularly preferred. In this blend, it is preferred to use two compounds according to the formula (I) with one compound of the formula (II), or two compounds according to the formula (II) with one compound of the formula (I).

The present invention also provides a colour photographic material containing cyanine dyes according to the formula (I), preferably according to the formulae (Ia), (Ib) and (Ic), in particular together with compounds of the formula (II). According to the invention, the cyanine dyes may be added to the colour photographic materials in conventional quantities, for example of 1 to 3000, preferably of 100 to 2000 and in particular of 200 to 900 $\mu$mol/mol of $AgNO_3$. The resultant colour photographic materials are distinguished by particularly elevated spectral sensitivity, which is substantially retained even after storage under extreme conditions (tropical conditions).

The present invention furthermore provides the use of the compounds of the formula (I) as spectral sensitisers.

Examples of colour photographic materials are colour negative films, colour reversal films, colour positive films, colour photographic paper, colour reversal photographic paper, colour-sensitive materials for the dye diffusion transfer process or the silver dye bleaching process. A review is given in Research Disclosure 37038 (1995) and Research Disclosure 38957 (1996).

The photographic materials consist of a support onto which at least one photosensitive silver halide emulsion layer is applied. Thin films and sheets are in particular suitable as supports. A review of support materials and the auxiliary layers applied to the front and reverse sides of which is given in Research Disclosure 37254, part 1 (1995), page 285 and in Research Disclosure 38957, part XV (1996), page 627.

The colour photographic materials conventionally contain at least one red-sensitive, one green-sensitive and one blue-sensitive silver halide emulsion layer, optionally together with interlayers and protective layers.

Depending upon the type of the photographic material, these layers may be differently arranged. This is demonstrated for the most important products:

Colour photographic films such as colour negative films and colour reversal films have on the support, in the stated sequence, 2 or 3 red-sensitive, cyan-coupling silver halide emulsion layers, 2 or 3 green-sensitive, magenta-coupling silver halide emulsion layers and 2 or 3 blue-sensitive, yellow-coupling silver halide emulsion layers. The layers of identical spectral sensitivity differ with regard to their photographic sensitivity, wherein the less sensitive sub-layers are generally arranged closer to the support than the more highly sensitive sub-layers.

A yellow filter layer is conventionally arranged between the green-sensitive and blue-sensitive layers which prevents blue light from reaching the underlying layers.

Possible options for different layer arrangements and the effects thereof on photographic properties are described in J. Inf. Rec. Mats., 1994, volume 22, pages 183–193 and in Research Disclosure 38957, part XI (1996), page 624.

Colour photographic paper, which is usually substantially less photosensitive than a colour photographic film, conventionally has on the support, in the stated sequence, one blue-sensitive, yellow-coupling silver halide emulsion layer, one green-sensitive, magenta-coupling silver halide emulsion layer and one red-sensitive, cyan-coupling silver halide emulsion layer; the yellow filter layer may be omitted.

The number and arrangement of the photosensitive layers may be varied in order to achieve specific results. For example, all high sensitivity layers may be grouped together in one package of layers and all low sensitivity layers may be grouped together in another package of layers in order to increase sensitivity (DE-25 30 645).

The substantial constituents of the photographic emulsion layers are binder, silver halide grains and colour couplers.

Details of suitable binders may be found in *Research Disclosure* 37254, part 2 (1995), page 286 and in *Research Disclosure* 38957, part II.A (1996), page 598.

Details of suitable silver halide emulsions, the production, ripening, stabilisation and spectral sensitisation thereof, including, for the purposes of the present invention, spectral sensitisers to be used in addition to the cyanine dyes according to the invention, may be found in *Research Disclosure* 37254, part 3 (1995), page 286, in *Research Disclosure* 37038, part XV (1995), page 89 and in *Research Disclosure* 38957, part V.A (1996), page 603.

For the purposes of the present invention, in a preferred embodiment, the emulsions used comprise tab-grain emulsions. These should be taken to mean emulsions containing tabular silver halide crystals with an aspect ratio of >2, wherein the aspect ratio is the ratio of the diameter of a circle of the same area as the projected surface area to the thickness of the crystal.

Photographic materials with camera sensitivity conventionally contain silver bromide-iodide emulsions, which may optionally also contain small proportions of silver chloride. Photographic print materials contain either silver chloride-bromide emulsions with up to 80 mol % of AgBr or silver chloride-bromide emulsions with above 90 mol % of AgCl, for example even more than 95 mol %, more than 98 mol % or even more than 99 mol % to 100 mol % of AgCl.

Details relating to colour couplers may be found in *Research Disclosure* 37254, part 4 (1995), page 288, in *Research Disclosure* 37038, part II (1995), page 80 and in *Research Disclosure* 38957, part X.B (1996), page 616. The maximum absorption of the dyes formed from the couplers and the developer oxidation product is preferably within the following ranges: yellow coupler 430 to 460 nm, magenta coupler 540 to 560 nm, cyan coupler 630 to 700 nm.

In order to improve sensitivity, grain, sharpness and colour separation in colour photographic films, compounds are frequently used which, on reaction with the developer oxidation product, release photographically active compounds, for example DIR couplers which eliminate a development inhibitor.

Details relating to such compounds, in particular couplers, may be found in *Research Disclosure* 37254, part 5 (1995), page 290, in *Research Disclosure* 37038, part XIV (1995), page 86 and in *Research Disclosure* 38957, part X.C (1996), page 618.

Colour couplers, which are usually hydrophobic, as well as other hydrophobic constituents of the layers, are conventionally dissolved or dispersed in high-boiling organic solvents. These solutions or dispersions are then emulsified into an aqueous binder solution (conventionally a gelatine solution) and, once the layers have dried, are present in the layers as fine droplets (0.05 to 0.8 μm in diameter).

Suitable high-boiling organic solvents, methods for the introduction thereof into the layers of a photographic material and further methods for introducing chemical compounds into photographic layers may be found in *Research Disclosure* 37254, part 6 (1995), page 292.

The non-photosensitive interlayers generally located between layers of different spectral sensitivity may contain agents which prevent an undesirable diffusion of developer oxidation products from one photosensitive layer into another photosensitive layer with a different spectral sensitisation.

Suitable compounds (white couplers, scavengers or DOP scavengers) may be found in *Research Disclosure* 37254, part 7 (1995), page 292, in *Research Disclosure* 37038, part III (1995), page 84 and in *Research Disclosure* 38957, part X.D (1996), pages 621 et seq.

The photographic material may also contain UV light absorbing compounds, optical brighteners, spacers, filter dyes, formalin scavengers, light stabilisers, anti-oxidants, $D_{min}$ dyes, plasticisers (latices), biocides and additives to improve coupler and dye stability, to reduce colour fogging and to reduce yellowing and others. Suitable compounds may be found in *Research Disclosure* 37254, part 8 (1995), page 292, in *Research Disclosure* 37038, parts IV, V, VI, VII, X, XI and XIII (1995), pages 84 et seq. and in *Research Disclosure* 38957, parts VI, VIII, IX and X (1996), pages 607 and 610 et seq.

The layers of colour photographic materials are conventionally hardened, i.e. the binder used, preferably gelatine, is crosslinked by appropriate chemical methods.

Suitable hardener substances may be found in *Research Disclosure* 37254, part 9 (1995), page 294, in *Research Disclosure* 37038, part XII (1995), page 86 and in *Research Disclosure* 38957, part II.B (1996), page 599.

Once exposed with an image, colour photographic materials are processed using different processes depending upon their nature. Details relating to processing methods and the necessary chemicals are disclosed in *Research Disclosure* 37254, part 10 (1995), page 294, in *Research Disclosure* 37038, parts XVI to XXIII (1995), pages 95 et seq. and in *Research Disclosure* 38957, parts XVIII, XIX and XX (1996), pages 630 et seq. together with example materials.

EXAMPLES

Example 1

Crude Emulsion

A solution of 144 g of inert gelatine and 107 g of potassium bromide in 18 kg of water was initially introduced with stirring. At 30° C., an aqueous silver nitrate solution (47 g of silver nitrate in 550 g of water) and an aqueous halide solution (33 g of potassium bromide in 550 g of water) were then apportioned as a twin inflow within 30 seconds. 395 g of inert gelatine in 4 kg of water were then added. After heating to 74° C., an aqueous silver nitrate solution (114 g of silver nitrate in 1.4 kg of water) was then added within 20 minutes.

The second twin inflow was then performed, likewise at 74° C. In this operation, an aqueous silver nitrate solution (1339 g of silver nitrate in 8.3 kg of water) and an aqueous halide solution (1117 g of potassium bromide in 9.8 kg of water) were apportioned within 50 minutes with a rising feed rate. The feed rate was here raised in 10 steps from an initial value of 70 ml/minute to 400 ml/minute. The pBr value of 2.3 in the dispersion medium was held constant during the inflow.

After the final inflow, the emulsion was cooled to 25° C., flocculated at pH 3.5 by addition of polystyrenesulfonic acid and then washed at 20° C. The flocculate was then redispersed with water, made up to 7.5 kg and redispersed at pH 6.5 and a temperature of 50° C.

The emulsion contained a fraction of above 80% (relative to the projected surface area of the crystals) of hexagonal lamellae having an aspect ratio (average diameter of a circle of the same area as the projected surface area/thickness of the lamellae) of 8 and an adjacent edge ratio of 1:1 to 1.5:1. The grain size was 0.55 μm and the distribution range 18%.

The silver halide emulsion was chemically ripened at 55° C., pAg 7.4 and pH 6.5 with 5.0 μmol of tetrachloroauric acid, 690 μmol of potassium thiocyanate and 20 μmol of sodium thiosulfate per mol of Ag.

After addition of 350 μmol of 4-hydroxy-6-methyl-1,3,3a,7-tetraazaindene per 100 g of Ag, the emulsion was spectrally sensitised by adding to the emulsion, which was at a temperature of 40° C., in each case 500 μmol of spectral sensitiser per mol of Ag dissolved in methanol or a mixture of methanol/phenoxyethanol and then stirring the mixture for a further 20 minutes at 40° C.

When sensitiser mixtures are used, the total is standardised in each case to 500 μmol/mol of Ag. The sensitiser stated first in Tables 5 and 6 was also added to the emulsion first, after 20 minutes' stirring at 40° C. the second stabiliser was added and optionally after a further 20 minutes at 40° C., the third was added.

The emulsion was combined with an emulsion of a magenta coupler M-1 and applied onto a 120 μm gauge film support of subbed cellulose acetate.

Each m² of the individual cast layers contains:

AgBr corresponding to
0.63 g of AgNO$_3$
1.38 g of gelatine
0.95 g of magenta coupler M-1
0.29 g of tricresyl phosphate The material was hardened by application of a protective layer prepared from 0.2 g of gelatine and 0.3 g of instant hardener (H-1) per m².

The sensitivities of the materials produced in this manner were determined. To this end, samples of the material were exposed behind a graduated wedge and subjected to colour negative processing according to *The Journal of Photographic Science,* 1974, pages 597, 598. The sensitisers used and the results are shown in Tables 1 to 3.

TABLE 1

| Spectral sensitisers | Sensitivity* | Decrease in sensitivity** | Type of sample |
|---|---|---|---|
| I-15 | 0.97 | 0.01 | Invention |
| I-16 | 0.99 | 0.02 | Invention |
| I-18 | 1.00 | 0.02 | Invention |
| V-1 | 0.92 | 0.07 | Comparison |
| V-2 | 0.94 | 0.05 | Comparison |
| V-3 | 0.91 | 0.06 | Comparison |

*sensitivity standardised to that of I-18.
**determined as the difference between the initial sensitivity and the sensitivity after 7 days' storage (unexposed) under tropical conditions (35° C./90% relative atmospheric humidity)

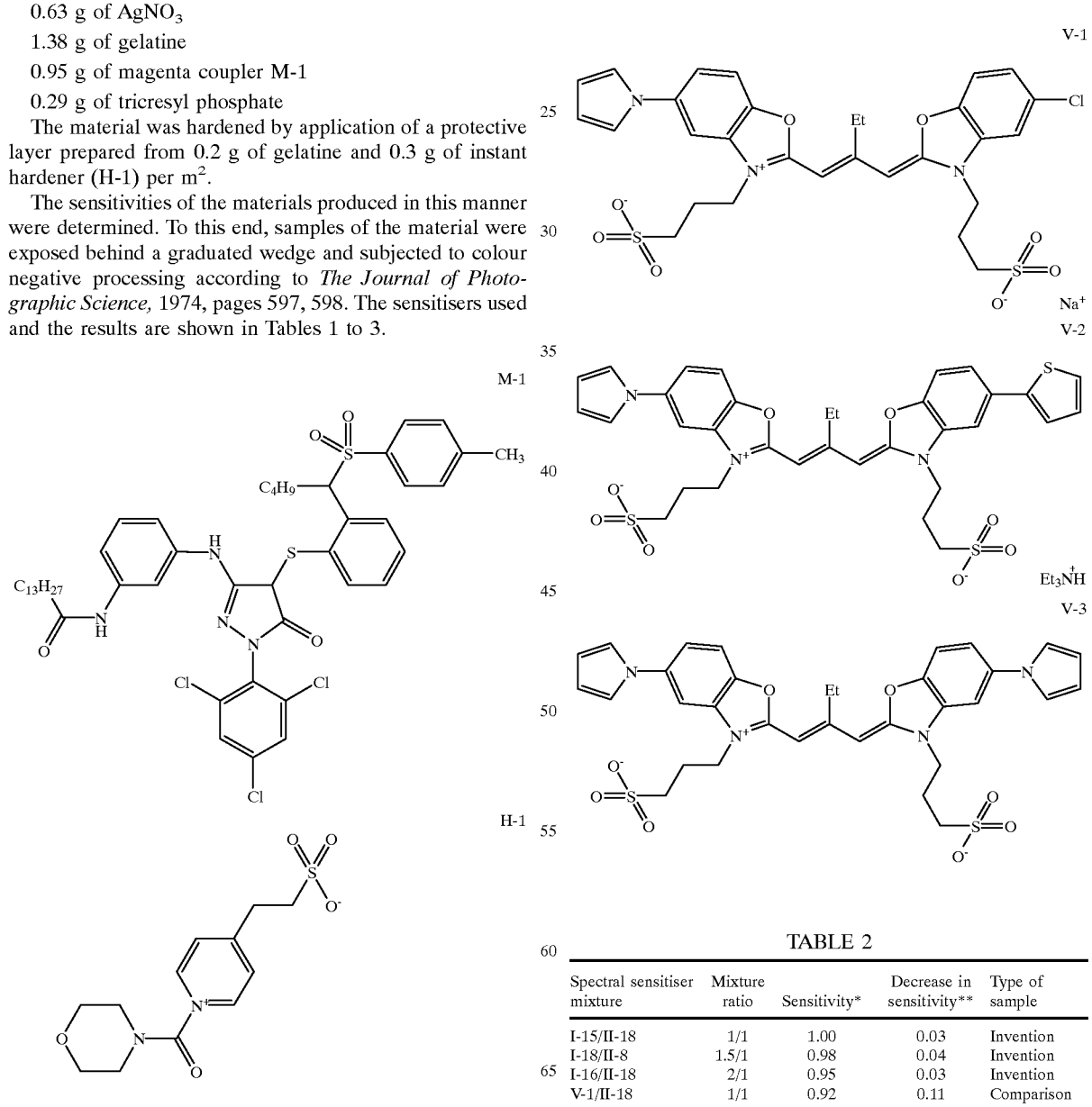

TABLE 2

| Spectral sensitiser mixture | Mixture ratio | Sensitivity* | Decrease in sensitivity** | Type of sample |
|---|---|---|---|---|
| I-15/II-18 | 1/1 | 1.00 | 0.03 | Invention |
| I-18/II-8 | 1.5/1 | 0.98 | 0.04 | Invention |
| I-16/II-18 | 2/1 | 0.95 | 0.03 | Invention |
| V-1/II-18 | 1/1 | 0.92 | 0.11 | Comparison |

TABLE 2-continued

| Spectral sensitiser mixture | Mixture ratio | Sensitivity* | Decrease in sensitivity** | Type of sample |
|---|---|---|---|---|
| V-2/II-8 | 1.5/1 | 0.90 | 0.10 | Comparison |
| V-3/II-18 | 2/1 | 0.87 | 0.08 | Comparison |

*sensitivity standardised to the combination I-15/II-18 = 1/1.
**determined as the difference between the initial sensitivity and the sensitivity after 7 days' storage (unexposed) under tropical conditions (35° C./90% relative atmospheric humidity)

TABLE 3

| Spectral sensitiser mixture | Mixture ratio | Sensitivity* | Decrease in sensitivity** | Type of sample |
|---|---|---|---|---|
| I-15/II-18/II-9 | 10/3/1 | 1.00 | 0.03 | Invention |
| I-16/II-18-II-9 | 10/3/1 | 0.96 | 0.04 | Invention |
| I-18/II-18/II-9 | 10/3/1 | 0.96 | 0.04 | Invention |
| I-15/II-18/II-9 | 52/17/1 | 0.98 | 0.01 | Invention |
| I-16/II-18/II-9 | 52/17/1 | 0.97 | 0.02 | Invention |
| I-18/II-18/II-9 | 52/17/1 | 0.97 | 0.02 | Invention |
| V-1/II-18/II-9 | 10/3/1 | 0.88 | 0.10 | Comparison |
| V-2/II-18/II-9 | 10/3/1 | 0.90 | 0.09 | Comparison |
| V-3/II-18/II-9 | 10/3/1 | 0.91 | 0.08 | Comparison |
| V-1/II-18/II-9 | 52/17/1 | 0.93 | 0.09 | Comparison |
| V-2/II-18/II-9 | 52/17/1 | 0.92 | 0.12 | Comparison |
| V-3/II-18/II-9 | 52/17/1 | 0.92 | 0.08 | Comparison |

*sensitivity standardised to that of I-15/II-18/II-9 = 10/3/1.
**determined as the difference between the initial sensitivity and the sensitivity after 7 days' storage (unexposed) under tropical conditions (35° C./90% relative atmospheric humidity)

Example 2

Preparation of the crude photographic emulsion, the ripening and spectral sensitisation thereof were performed as in Example 1, except that a mixture of cyan couplers BG-1 and BG-2 was used instead of the magenta coupler M-1.

Each $m^2$ of the individual cast layers contains:

AgBr corresponding to
  0.63 g of $AgNO_3$
  1.38 g of gelatine
  0.25 g of cyan coupler BG-1
  0.37 g of cyan coupler BG-2
  0.62 g of tricresyl phosphate The material was hardened by application of a protective layer prepared from 0.2 g of gelatine and 0.3 g of instant hardener (H-1) per $m^2$.

The sensitivities of the materials produced in this manner were determined. To this end, samples of the material were exposed behind a graduated wedge and subjected to colour negative processing according to *The Journal of Photographic Science*, 1974, pages 597, 598. The results are shown in Tables 4 and 5.

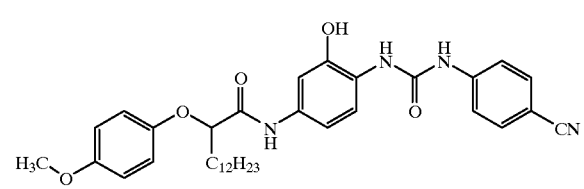

BG-1

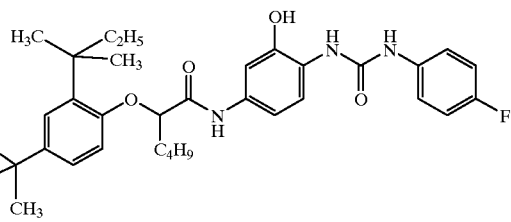

BG-2

TABLE 4

| Spectral sensitiser | Sensitivity* | Decrease in sensitivity** | Type of sample |
|---|---|---|---|
| I-24 | 0.97 | 0.03 | Invention |
| I-36 | 1.00 | 0.02 | Invention |
| V-4 | 0.92 | 0.11 | Comparison |
| V-5 | 0.94 | 0.14 | Comparison |

*sensitivity standardised to that of I-36.
**determined as the difference between the initial sensitivity and the sensitivity after 7 days' storage (unexposed) under tropical conditions (35° C./90% relative atmospheric humidity)

TABLE 5

| Spectral sensitiser mixture | Mixture ratio | Sensitivity* | Decrease in sensitivity** | Type of sample |
|---|---|---|---|---|
| I-36/II-13/II-14 | 1/3/0.5 | 0.97 | 0.02 | Invention |
| I-36/II-13/II-9 | 1/3/0.5 | 1.00 | 0.03 | Invention |
| I-36/II-15/II-14 | 1/2.8/0.15 | 0.96 | 0.04 | Invention |
| I-36/II-15/II-9 | 1/2.8/0.15 | 0.95 | 0.04 | Invention |
| V-4/II-13/II-14 | 1/3/0.5 | 0.91 | 0.10 | Comparison |
| V-4/II-13/II-9 | 1/3/0.5 | 0.88 | 0.08 | Comparison |
| V-4/II-15/II-14 | 1/2.8/0.15 | 0.85 | 0.07 | Comparison |
| V-4/II-15/II-9 | 1/2.8/0.15 | 0.90 | 0.07 | Comparison |

*sensitivity standardised to that of the combination I-36/II-13/II-9 = 1/3/0.5.
**determined as the difference between the initial sensitivity and the sensitivity after 7 days' storage (unexposed) under tropical conditions (35° C./90% relative atmospheric humidity)

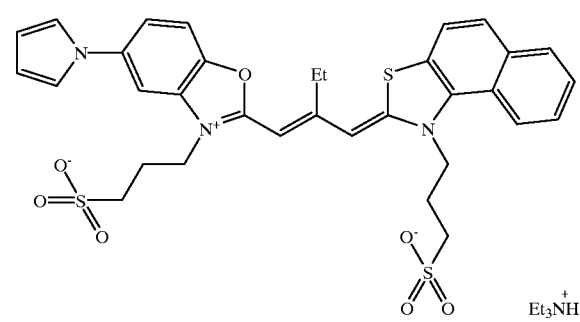

V-4

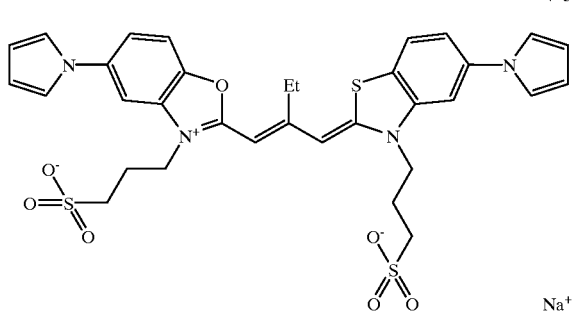

V-5

Example 3

Preparation of the crude photographic emulsion, the ripening and spectral sensitisation thereof were performed as in Example 1, except that yellow coupler G-1 was used instead of the magenta coupler M-1.

Each m² of the individual cast layers contains:

AgBr corresponding to
  0.63 g of $AgNO_3$
  0.78 g of gelatine
  0.78 g of G-1
  0.39 g of tricresyl phosphate The material was hardened by application of a protective layer prepared from 0.2 g of gelatine and 0.3 g of instant hardener (H-1) per m².

The sensitivities of the materials produced in this manner were determined. To this end, samples of the material were exposed behind a graduated wedge and subjected to colour negative processing according to *The Journal of Photographic Science*, 1974, pages 597, 598. The results are shown in Table 6.

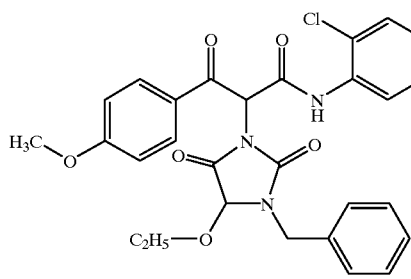

G-1

TABLE 6

| Spectral sensitiser | Sensitivity* | Decrease in sensitivity** | Type of sample |
|---|---|---|---|
| I-1 | 0.95 | 0.03 | Invention |
| I-5 | 1.00 | 0.01 | Invention |
| I-9 | 0.98 | 0.01 | Invention |
| V-6 | 0.86 | 0.05 | Comparison |

TABLE 6-continued

| Spectral sensitiser | Sensitivity* | Decrease in sensitivity** | Type of sample |
|---|---|---|---|
| V-7 | 0.92 | 0.07 | Comparison |
| V-8 | 0.93 | 0.09 | Comparison |

*sensitivity standardised to that of I-5.
**determined as the difference between the initial sensitivity and the sensitivity after 7 days' storage (unexposed) under tropical conditions (35° C./90% relative atmospheric humidity)

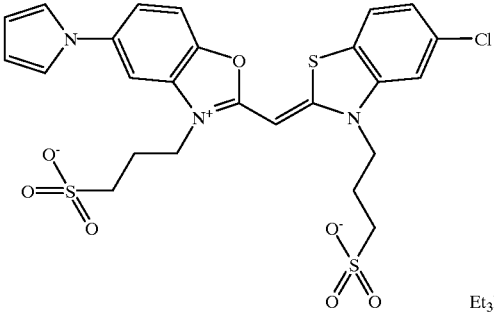

V-6

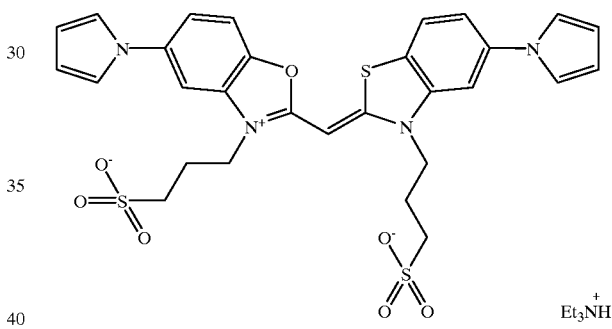

V-7

Example 4

Emulsion Production

The following solutions were prepared, in each case using demineralised water:

| Solution 1 | 1000 g water |
| | 140 g gelatine |
| Solution 2 | 1650 g water |
| | 360 g NaCl |
| | 0.11 mg $Na_3RhCl_6$ |
| Solution 3 | 1600 g water |
| | 1000 g $AgNO_3$ |

Solutions 2 and 3 were simultaneously added at 60° C. with vigorous stirring to solution 1 over the course of 105 minutes at a pAg of 7.7. A silver chloride emulsion having an average particle diameter of 0.40 μm was formed. The gelatine/$AgNO_3$ weight ratio is 0.14. The emulsion was ultrafiltered, washed and redispersed with such a quantity of gelatine that the gelatine/$AgNO_3$ weight ratio was 0.56.

Ripening and Sensitisation

The emulsion was ripened at a pH of 5.3 with an optimum quantity of gold(III) chloride and $Na_2S_2O_3$ for 3 hours at a temperature of 60° C. After chemical ripening, the emulsion was spectrally sensitised at 50° C. with 2.58 mmol of spectral sensitiser/kg of Ag and stabilised with 1.0 g of compound (ST)/kg of Ag. 0.3 mol of KBr/mol of AgNO$_3$ were then added.

Each m$^2$ of the individual cast layers contained:

| AgCl corresponding to | 0.30 g of AgNO$_3$ |
|---|---|
| | 0.66 g of gelatine |
| | 0.20 g of PP-1 |
| | 0.10 g of SC-1 |
| | 0.25 g of coupler solvent K-1 |
| | 0.05 g of dye stabiliser ST-2 |

The material was hardened by application of a protective layer prepared from 0.92 g of gelatine and 0.34 g of instant hardener (H-1) per m$^2$.

The resultant sample was exposed for 40 ms behind a step wedge and processed as follows using process AP 94:

Colour developer - 45 s - 35° C.

| Triethanolamine | 9.0 g |
|---|---|
| N,N-diethylenehydroxylamine | 4.0 g |
| Diethylene glycol | 0.05 g |
| 3-Methyl-4-amino-N-ethyl-N-methanesulfonaminoethylaniline sulfate | 5.0 g |
| Potassium sulfite | 0.2 g |
| Triethylene glycol | 0.05 g |
| Potassium carbonate | 22 g |
| Potassium hydroxide | 0.4 g |
| Ethylenediaminetetraacetic acid, disodium salt | 2.2 g |
| Potassium chloride | 2.5 g |
| 1,2-Dihydroxybenzene-3,4,6-trisulfonic acid, sodium salt | 0.3 g | make up with water to 1000 ml (pH = 10.0).
Bleach/fixing bath - 45 s - 35° C.

| Ammonium thiosulfate | 75 g |
|---|---|
| Sodium hydrogen sulfite | 13.5 g |
| Ammonium acetate | 2.0 g |
| Ethylenediaminetetraacetic acid (iron/ammonium salt) | 57 g |
| Ammonia, 25 wt. % | 9.5 g | make up with acetic acid to 1000 ml (pH = 5.5)
Rinsing: 2 min - 33° C.

Drying

The green sensitivity values determined from the material produced in this manner are shown in Table 7.

TABLE 7

| Spectral sensitiser | Sensitivity* | Decrease in sensitivity** | Type of sample |
|---|---|---|---|
| I-14 | 0.98 | 0.02 | Invention |
| I-15 | 0.96 | 0.02 | Invention |
| I-16 | 1.00 | 0.02 | Invention |
| II-3 | 0.93 | 0.05 | Comparison |
| V-9 | 0.94 | 0.05 | Comparison |
| V-10 | 0.93 | 0.06 | Comparison |

*sensitivity standardised to that of I-16.
**determined as the difference between the initial sensitivity and the sensitivity after 7 days' storage (unexposed) under tropical conditions (35° C./90% relative atmospheric humidity)

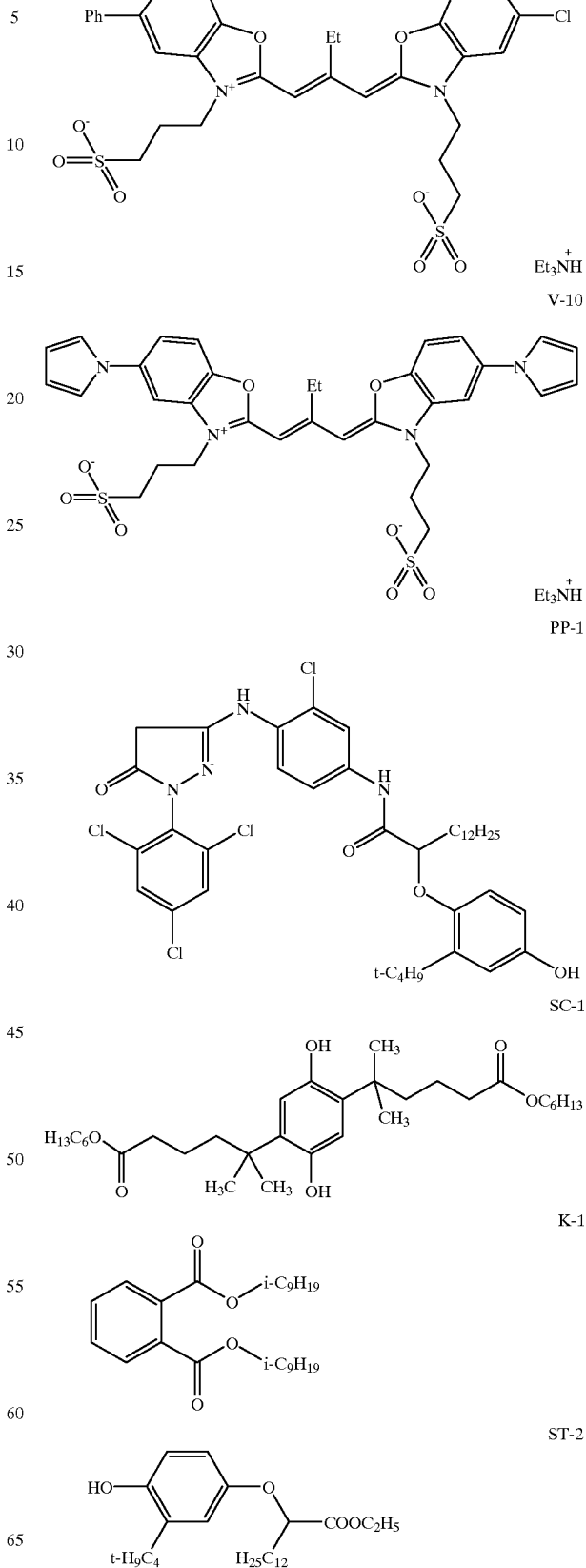

ST

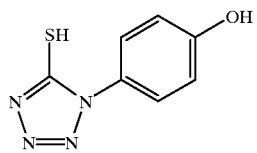

Example 5

| Emulsion production | |
|---|---|
| Solution 1 | 1100 g water |
| | 140 g gelatine |
| Solution 2 | 1860 g water |
| | 360 g NaCl |
| Solution 3 | 1800 g water |
| | 1000 g AgNO$_3$ |

Solutions 2 and 3 were simultaneously added at 50° C. with vigorous stirring to solution 1 over the course of 300 minutes at a pAg of 7.7. A silver chloride emulsion having an average particle diameter of 0.85 μm was obtained. The gelatine/AgNO$_3$ weight ratio is 0.14. The emulsion was ultrafiltered, washed and redispersed with such a quantity of gelatine that the gelatine/AgNO$_3$ weight ratio was 0.56.

Ripening and Sensitisation

The emulsion was ripened at a pH of 5.3 with an optimum quantity of gold(III) chloride and Na$_2$S$_2$O$_3$ at a temperature of 50° C. After chemical ripening, the emulsion was spectrally sensitised at 50° C. with 2.54 mmol of spectral sensitiser/kg of Ag, stabilised with 0.5 g of compound ST-3/kg of Ag and then combined with 0.6 mol % of KBr (relative to silver nitrate).

Each m$^2$ of the individual cast layers contained:

AgCl corresponding to
0.40 g of AgNO$_3$
0.96 g of gelatine
0.55 g of yellow coupler Y-1
0.21 g of tricresyl phosphate
0.11 g of dye stabiliser STA The material was hardened by application of a protective layer prepared from 0.92 g of gelatine and 0.34 g of instant hardener (H-1) per m$^2$.

Exposure and development were performed as in Example 5.

The blue sensitivity values determined from the material produced in this manner are shown in Table 8.

TABLE 8

| Spectral sensitiser | Sensitivity* | Decrease in sensitivity** | Type of sample |
|---|---|---|---|
| I-1 | 0.96 | 0.03 | Invention |
| I-5 | 0.99 | 0.02 | Invention |
| I-9 | 1.00 | 0.02 | Invention |
| V-6 | 0.88 | 0.04 | Comparison |
| V-7 | 0.91 | 0.07 | Comparison |
| V-8 | 0.92 | 0.08 | Comparison |

*sensitivity standardised to that of I-9.
**determined as the difference between the initial sensitivity and the sensitivity after 7 days' storage (unexposed) under tropical conditions (35° C./90% relative atmospheric humidity)

ST-3

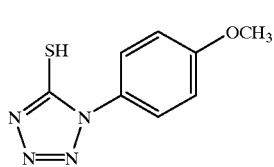

Y-1

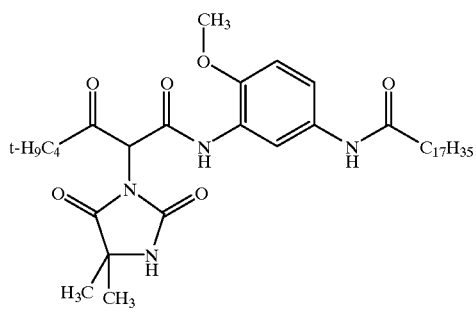

-continued

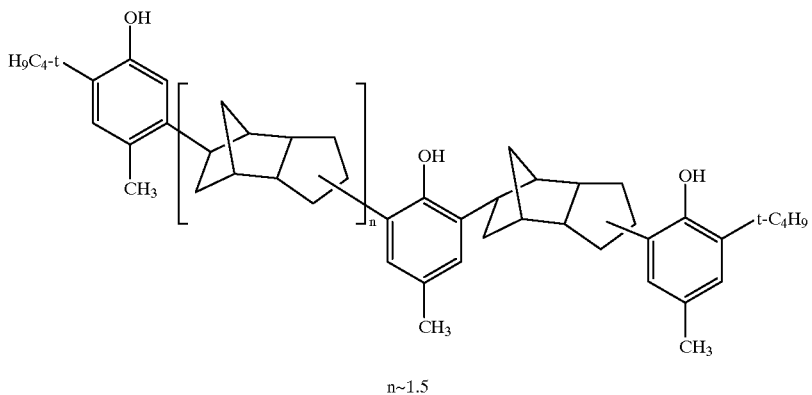

n~1.5

STA

What is claimed is:

1. A color photographic silver halide material which comprises at least one photosensitive silver halide emulsion, and a cyanine dye of the formula (I)

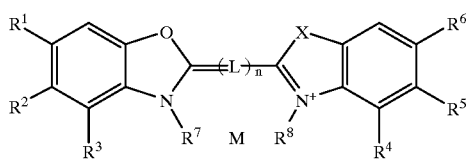
(I)

in which $R^1$, $R^2$, $R^3$, $R^4$, $R^5$ and $R^6$ mutually independently denote a substituent, providing at least one of the residues $R^1$, $R^2$, $R^3$ denotes an indolyl substituent, X denotes O, S, Se, $NR^9$, CH=CH or $C(CH_3)_2$, wherein $R^9$ denotes a optionally substituted alkyl residue, $R^7$ and $R^8$ and mutually independently denote alkyl, sulfoalkyl, carboxyalkyl, $-(CH_2)_l-SO_2-Y-SO_2$-alkyl, $-(CH_2)_l-SO_2-Y-CO$-alkyl, $-(CH_2)_l-CO-Y-SO_2$-alkyl, $-(CH_2)_l-CO-Y-O$-alkyl or $-(CH_2)_l-NH-SO_3^\ominus$, $-(CH_2)_l-N(alkyl)-SO_3^\ominus$, or $-(CH_2)_l-N(aryl)-SO_3^\ominus$, providing that l=1 to 6 and Y means NH or $N^-$, n means 1, 3, 5 or 7, L denotes a substituted or unsubstituted methine group, which may be a constituent of one or more carbocyclic rings, and M denotes a counterion optionally necessary to equalize charges.

2. The color photographic silver halide material according to claim 1, wherein said dye of formula I is at least one cyanine dye of the formulae (Ia), (Ib) and (Ic)

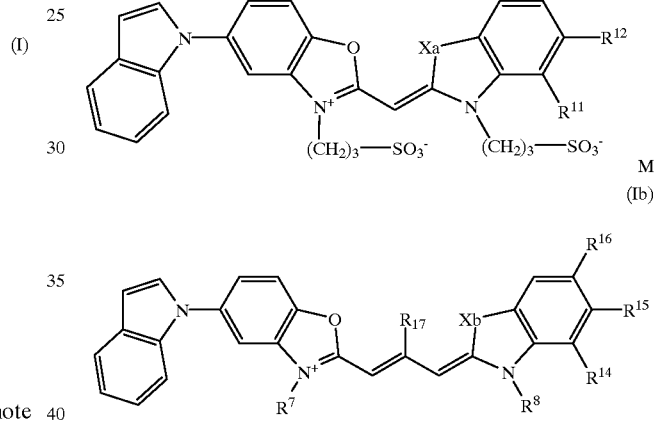

in which $X_a$, $X_b$, and $X_c$ denote O, S, Se, $NR^9$, CH=CH or $C(CH_3)_2$, wherein $R^9$ denotes an optionally substituted alkyl residue;

$R^{11}$ to $R^{16}$ and $R^{18}$ to $R^{20}$ denote a substituent, $R^{11}$ and $R^{12}$, or $R^{12}$ and $R^{13}$, or $R^{14}$ and $R^{15}$, or $R^{15}$ and $R^{16}$, or $R^{18}$ and $R^{19}$, or $R^{19}$ and $R^{20}$ may be a constituent of a fused benzo or naphtho ring, $R^{17}$ denotes H, $CH_3$ or $C_2H_5$ $R^{21}$ denotes halogen, $N(alkyl)_2$, N-piperidinyl, -pyrrolidinyl, N-pyrrolyl, S-alkyl, or $S(CH_2)_mCOOH$, providing that m denotes 1, 2, 3, 4, 5 or 6.

$R^{22}$ and $R^{23}$ are identical of different and are H or alkyl, carboxylic acid or carboxylic acid ester residues, $R^7$ and $R^8$ have the above-stated meaning M where required, denote a counterion.

3. The color photographic silver halide material according to claim 1, which further comprises at least one cyanine dye of the formula (II)

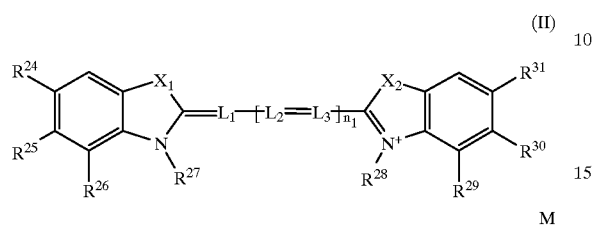

wherein
- $X_1$ and $X_2$ mutually independently denote O, S, Se, $NR^9$, $C(CH_3)_2$ or CH=CH, wherein $R^9$ denotes an optionally substituted alkyl residue,
- $R^{27}$ and $R^{28}$ mutually independently denote alkyl, sulfoalkyl, carboxyalkyl, $l-(CH_2)_l-SO_2-Y-SO_2$-alkyl, $-(CH_2)_l-SO_2-Y-CO$-alkyl, $-(CH_2)_l-CO-Y-SO_2$-alkyl or $-(CH_2)_l-CO-Y-O$-alkyl, providing that l=1 to 6 and Y means NH or $N^-$,
- $R^{24}$, $R^{25}$, $R^{26}$, $R^{29}$, $R^{30}$, and $R^{31}$ mutually independently denote halogen, H, alkyl, alkoxy, phenyl, 2-thienyl, 3-thienyl, 1-pyrrolyl, 2-furanyl, 3-furanyl, CN, $CF_3$ or aryl; or $R^{24}$, together with $R^{25}$, or $R^{25}$ together with $R^{26}$, or $R^{29}$ together with $R^{30}$, or $R^{30}$ a together with $R^{31}$ denote the remaining members to complete an optionally substituted fused benzo or naphtho ring system,
- $n_1$ means 0 or 1
- $L_1$, $L_2$ and $L_3$ mutually independently denote substituted or unsubstituted methine groups and
- M denotes a counterion optionally necessary to equalize charges.

4. The color photographic silver halide material according to claim 1, wherein the cyanine dyes according to the formulae (I) and (II) are present in a mixture ratio to 0.1:10 to 10:0.1.

5. The color photographic silver halide material according to claim 3, wherein a cyanine dye according to the formula (I) is used with two cyanine dyes according to the formula (II).

6. The color photographic silver halide material according to claim 3, wherein a cyanine dye according to the formula (II) is used with two cyanine dyes according to the formula (I).

7. The color photographic silver halide material according to claim 1, which further comprises tab-grain emulsions.

8. The color photographic silver halide material according to claim 2, wherein $X_a$ is S or O and $X_b$ is O, S, $N-C_2H_5$, or Se and $X_c$ is S, Se or O,
- $R^{11}$ to $R^{16}$ and $R^{18}$ to $R^{20}$ and denote H; halogen; a substituted or unsubstituted 1-pyrrolyl, 2-pyrrolyl, 3-pyrrolyl, 2-thienyl, 3-thienyl, N-indolyl, phenyl, 2-furanyl, 3-furanyl or alkyl;
- $R^{11}$ and $R^{12}$ or $R^{12}$ and $R^{13}$ or $R^{14}$ and $R^{16}$ or $R^{18}$ and $R^{19}$ or $R^{19}$ and $R^{20}$ may be a constituent of a fused benzo or naphtho ring,
- $R^{17}$ denotes H, $CH_3$ or $C_2H_5$

- $R^{21}$ denotes Cl, $N(alkyl)_2$, N-piperidinyl, N-pyrrolidinyl, N-pyrrolyl, $SCH_3$ or $S(CH_2)_m$ COOH providing that m denotes 1, 2, 3, 4, 5 or 6,
- $R^{22}$ and $R^{23}$ are identical or different and denote hydrogen, methyl, carboxylic acid or carboxylic acid ester residues and
- M where required is $Na^+$, $EtN^+H$, tosylate or $I^-$.

9. The color photographic silver halide material according to claim 1, wherein n is 1, L is=C—, when n is 3, L is

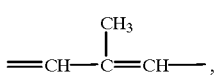

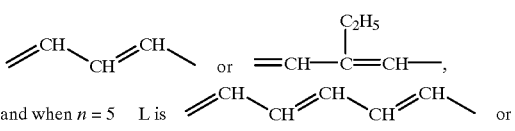

and when $n = 5$  L is 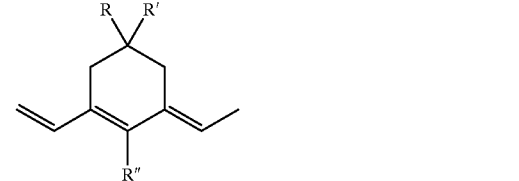 or wherein R and R' independently are H or alkyl and R" is H, halogen, $N(alkyl)_2$, $N(aryl)_2$, 5-membered nitrogenous heterocyclics or S-alkyl and when n=7, L is

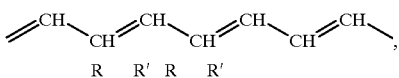

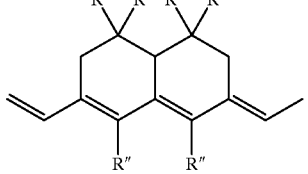

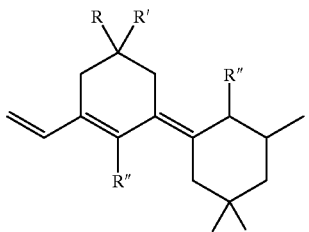 or

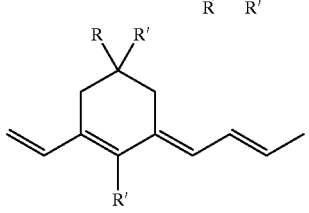

where R, R' and R" are defined above.

* * * * *